United States Patent
Gras et al.

(10) Patent No.: US 11,406,414 B2
(45) Date of Patent: Aug. 9, 2022

(54) ULTRASONIC CUTTING TIP FOR LUMBAR PROCEDURES

(71) Applicant: Stryker European Operations Holdings LLC, Kalamazoo, MI (US)

(72) Inventors: Guillaume Gras, Muenchenbuchsee (CH); Conor McCarthy, Ballineen (IE)

(73) Assignee: Stryker European Operations Holdings LLC, Kalamazoo, MI (US)

(*) Notice: Subject to any disclaimer, the term of this patent is extended or adjusted under 35 U.S.C. 154(b) by 229 days.

(21) Appl. No.: 16/661,923

(22) Filed: Oct. 23, 2019

(65) Prior Publication Data
US 2020/0121352 A1 Apr. 23, 2020

Related U.S. Application Data

(60) Provisional application No. 62/749,587, filed on Oct. 23, 2018.

(51) Int. Cl.
*A61B 17/32* (2006.01)

(52) U.S. Cl.
CPC ........... *A61B 17/320068* (2013.01); *A61B 2017/320077* (2017.08); *A61B 2017/320082* (2017.08); *A61B 2560/0418* (2013.01)

(58) Field of Classification Search
CPC A61B 2017/320082; A61B 17/320068; A61B 2560/0418; A61B 2017/320077; A61B 2017/320078; A61B 17/32; A61B 17/22012; A61B 2017/32007; A61B 2017/320072; A61B 2017/320073; A61B 2017/320074; A61B 2017/320075;
(Continued)

(56) References Cited

U.S. PATENT DOCUMENTS 4,974,581 A   12/1990  Wiksell
5,203,865 A    4/1993  Siepser
(Continued)

OTHER PUBLICATIONS

Cappabiance, M.D., Paolo et al., "Bone Removal With a New Ultrasonic Bone Curette During Endoscopic Endonasal Approach to the Seller-Supraseller Area: Technical Note", https://academic.cup.com/ons/article-abstract/66/suppl_1/ons-E118/2408898, p. ons-E118, Operative Neurosurgery, vol. 66, Issue Suppl_1, Mar. 1, 2010, 2 pages.
(Continued)

*Primary Examiner* — Robert A Lynch
(74) *Attorney, Agent, or Firm* — Howard & Howard Attorneys PLLC

(57) ABSTRACT

An ultrasonic tip and methods of operating the same. The ultrasonic tip comprises a shaft including a base and a flexible body. The body comprises a first portion and a second portion. The body is coupled to the base at the first portion and extends from the first portion to the second portion along a longitudinal axis. The second portion includes a cutting portion comprising a neck, and a head extending radially from the longitudinal axis. The head is coupled to the neck. A circular aperture is disposed between the head and the neck to define an inner circumferential surface. The head and the neck form an outer circumferential surface comprising a plurality of cutting teeth, the outer circumferential surface having a first thickness at the head that is greater than a second thickness at the neck.

19 Claims, 9 Drawing Sheets

(58) Field of Classification Search
CPC ... A61B 17/16; A61B 17/1659; A61B 17/142; A61B 17/147; A61B 17/149; A61B 2017/320004; A61C 1/07; A61C 3/03
See application file for complete search history.

(56) References Cited

U.S. PATENT DOCUMENTS

| | | | |
|---|---|---|---|
| 5,263,957 | A | 11/1993 | Davison |
| 5,324,299 | A | 6/1994 | Davison et al. |
| 5,342,380 | A | 8/1994 | Hood |
| 5,449,370 | A | 9/1995 | Vaitekunas |
| 5,695,510 | A | 12/1997 | Hood |
| 5,746,756 | A | 5/1998 | Bromfield et al. |
| 6,159,176 | A | 12/2000 | Broadwin et al. |
| 6,379,371 | B1 | 4/2002 | Novak et al. |
| 6,443,969 | B1 | 9/2002 | Novak et al. |
| 6,799,729 | B1 | 10/2004 | Voic |
| D551,764 | S | 9/2007 | Easley |
| 8,328,738 | B2 | 12/2012 | Frankhouser et al. |
| 8,343,178 | B2 | 1/2013 | Novak et al. |
| 8,353,912 | B2 | 1/2013 | Darian et al. |
| 8,512,340 | B2 | 8/2013 | Easley et al. |
| 8,911,460 | B2 | 12/2014 | Neurohr et al. |
| 9,387,005 | B2 | 7/2016 | Voic |
| 9,693,793 | B2 | 7/2017 | Akagane |
| 9,788,852 | B2 | 10/2017 | Voic |
| 10,206,704 | B2 | 2/2019 | Voic et al. |
| 2003/0204199 | A1 | 10/2003 | Novak et al. |
| 2009/0326535 | A1* | 12/2009 | Blus ............... A61B 17/142 606/80 |
| 2010/0130867 | A1* | 5/2010 | Vercellotti ......... A61C 17/20 600/459 |
| 2010/0168741 | A1 | 7/2010 | Sanai et al. |
| 2013/0103066 | A1 | 4/2013 | Rad |
| 2013/0204285 | A1* | 8/2013 | Gouery .......... A61B 17/320068 606/169 |
| 2014/0088597 | A1* | 3/2014 | Dibart ............. A61B 17/1673 606/79 |
| 2014/0276849 | A1 | 9/2014 | Voic |
| 2015/0005795 | A1* | 1/2015 | Darian .......... A61B 17/320068 606/169 |
| 2017/0319226 | A1 | 11/2017 | Voic et al. |

OTHER PUBLICATIONS

Abstract of Chang, HS, et al., "Ultrasonic Bone Curettage for Optic Canal Unroofing and Anterior Clinoidectomy-Technical Note", https://www.ncbi.nlm.nih.gov/pubmed/16619669, pp. 621-624, J. Neurosurg., vol. 104, No. 4, 2006, 1 page.

Ito, M.D., Kiyoshi et al., "Safe and Minimally Invasive Laminoplastic Laminotomy Using an Ultrasonic Bone Curette for Spinal Surgery: Technical Note", https://www.sciencedirect.com/science/article/pii/S0090301909000810, Surgical Neurolgy, vol. 72, No. 5, Nov. 2009, pp. 470-475.

Abstract of Kamiyama, T. et al., "Laparoscopic Hepatectomy with the Hook Blade of Ultrasonic Coagulating Shears and Bipolar Cautery with a Saline Irrigation System", https://www.ncbi.nlm.nih.gov/pubmed/15754100, pp. 49-54, J. Hepatobiliary Pancreat. Surg., 2005, 2 pages.

Matsuoka, H, "Recapping Hemilaminoplasty for Spinal Surgical Disorders Using Ultrasonic Bone Curette", https://www.ncbi.nlm.nih.gov/pubmed/22754735, Surgical Neurology International, Jun. 19, 2012, 6 pages.

Misonix "Bone Scalpel Webpage", http://misonix.com/products/bone-scalpel/, 2018, 3 pages.

Nakagawa, H. et al., "Technical Advantages of an Ultrasonic Bone Curette in Spinal Surgery", https://www.ncbi.nlm.nih.gov/pubmed/15871482, J. Neurosurg. Spine, vol. 2, No. 4, Apr. 2005, pp. 431-435.

Taylor, M.D., Jesse A. et al., "Endoscopically Assisted Le Fort I Osteotomy Using An Ultrasonic Scalpel: A Feasibility Study in Cadavers", https://www.sciencedirect.com/science/article/pii/S0278239109001736, pp. 1420-1424, Journal of Oral and Maxillofacial Surgery, vol. 67, No. 7, Jul. 2009, 2 pages.

Taylor, M.D., Jesse A. et al., "Endoscopically Assisted Le Fort III Osteotomy Using An Ultrasonic Scalpel: A Feasibility Study in Cadavers", https://journals.lww.eom/jcraniofacialsurgery/Abstract/2009/11000/Endoscopically_Assisted_Le_Fort_III_Osteotomy.54.aspx, pp. 2211-2214, Journal of Craniofacial Surgery, vol. 20, No. 6, Nov. 2009, 3 pages.

Abstract of Ueki, Koichiro et al., "Le Fort I Osteotomy Using an Ultrasonic Bone Curette to Fracture the Pterygoid Plates", pp. 381-386, https://www.ncbi.nlm.nih.gov/pubmed/15555522, Science Direct, Journal of Cranio-Maxillofacial Surgery, vol. 32, Issue 6, Dec. 2004, 1 page.

Abstract of Ueki, K. et al., "Use of the Sonopet Ultrasonic Curettage Device in Intraoral Vertical Ramus Osteotomy", pp. 745-747, https://www.sciencedirect.com/science/article/pii/S0901502707000926, Science Direct, International Journal of Oral and Maxillofacial Surgery, vol. 36, No. 8, Aug. 2007, 2 pages.

* cited by examiner

ULTRASONIC CUTTING TIP FOR LUMBAR PROCEDURES

RELATED APPLICATION

The present application claims the benefit of U.S. Provisional Patent Application No. 62/749,587, filed on Oct. 23, 2018, the entire disclosure of which is hereby incorporated by reference.

TECHNICAL FIELD

The present disclosure is generally directed to surgical instruments, and more specifically, ultrasonic cutting tips for cutting bone and other tissue.

BACKGROUND

In a surgical procedure it is sometimes necessary to use a cutting tip to remove tissue, including bone and cartilage. Such cutting tips and their accompanying blade body must be both strong and aggressive enough to cut bone, for applications such as use in lumbar procedures. However, aggressive use of existing cutting tips may sometimes lead to high stress and breakage. Additionally, at higher tip displacements, heat generation at the bone/tissue site is problematic, and therefore adequate cooling at the site is essential to avoid tissue damage.

Therefore, a need exists in the art for an ultrasonic cutting tip that overcomes one or more of the aforementioned disadvantages.

SUMMARY

The present disclosure relates to ultrasonic cutting tips for cutting bone and other tissue. In one embodiment, an ultrasonic tip comprises a shaft including base and a body. The body comprises a first portion and a second portion, wherein the body is coupled to the base at the first portion and said body extends from said first portion to said second portion along a longitudinal axis. The second portion includes a cutting portion comprising a neck, and a head extending radially from the longitudinal axis, and coupled to the neck. A circular aperture is disposed between the head and the neck to define an inner circumferential surface.

In another embodiment, an ultrasonic tip comprises a shaft including a base and a body. The base has a circular-shaped cross-section. The body comprises a first portion and a second portion. The body is coupled to the base at the first portion and the body extends from the first portion to the second portion along a longitudinal axis. The second portion includes a cutting portion. The body has a rectangular-shaped cross-section on an axis that is perpendicular to the longitudinal axis at the first portion and at the second portion. A first height of the rectangular-shaped cross-section at the first portion is at least three times greater than a first width of the rectangular-shaped cross section. A second height of the rectangular-shaped cross-section at the second portion is at least three times greater than a second width of the rectangular shaped cross-section. The first height is greater than the second height.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
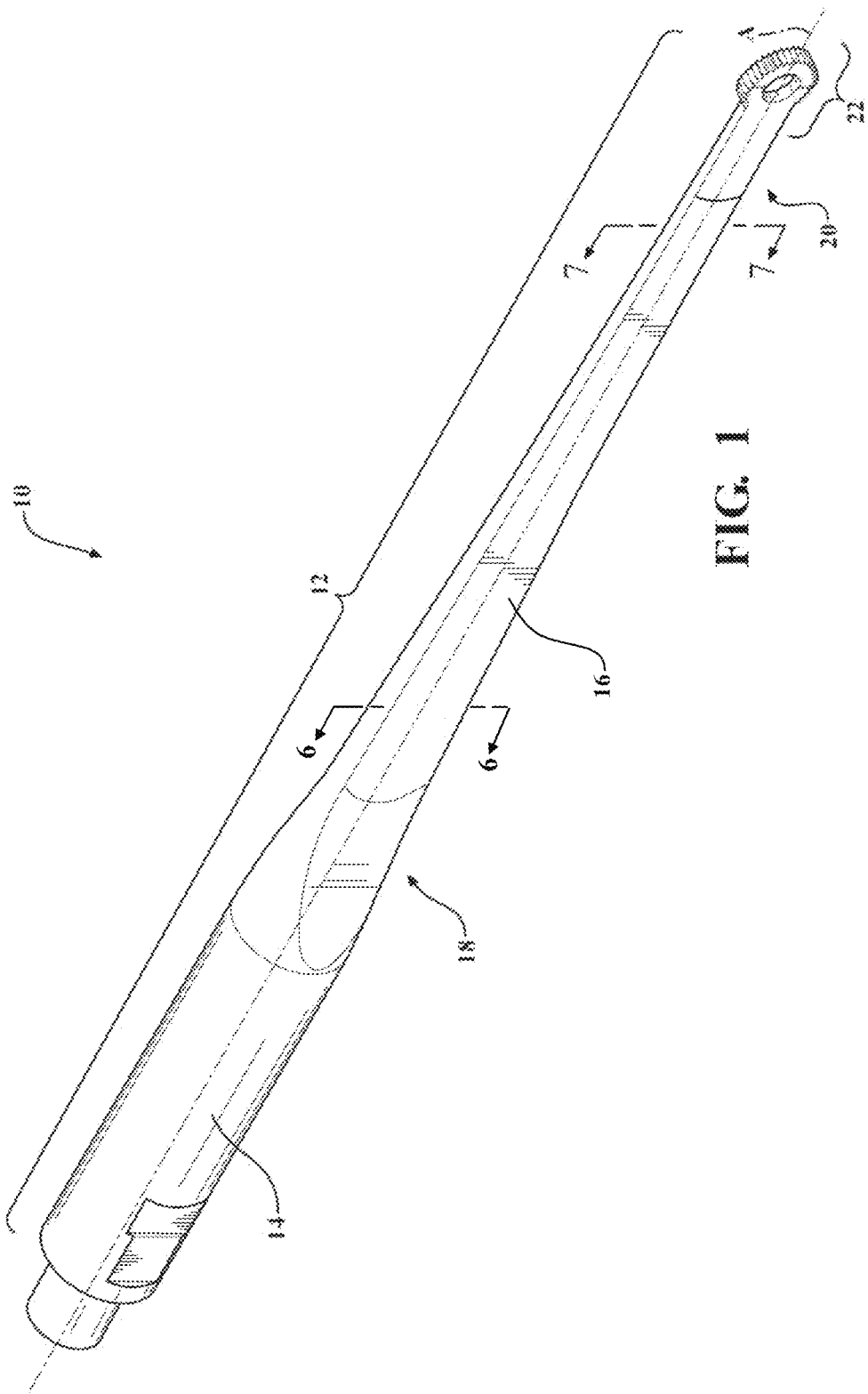
FIG. 1 is a perspective view of one embodiment of an ultrasonic tip.

FIG. 1 shows a perspective view of an ultrasonic tip 10. The ultrasonic tip 10 comprises a shaft 12, which includes a base 14 and a body 16. In one configuration, the shaft 12 may be integral, unitary, and one-piece. The base 14 may be cylindrical and have a circular-shaped cross-section. The body 16 may be solid, having no lumen or other hollow channel for aspiration. The base 14 may include threads or other features for coupling to an ultrasonic handpiece at the proximal end. The body 16 comprises a first portion 18 and a second portion 20. The body 16 is coupled to the base 14 at the first portion 18, which has a different cross-sectional shape than the base 14, and extends from the first portion 18 to the second portion 20 along a longitudinal axis A. The second portion 20 includes a cutting portion 22. The cutting portion 22 may have a circular shape, a semi-circular shape, or a D-shape.

Figure 2:
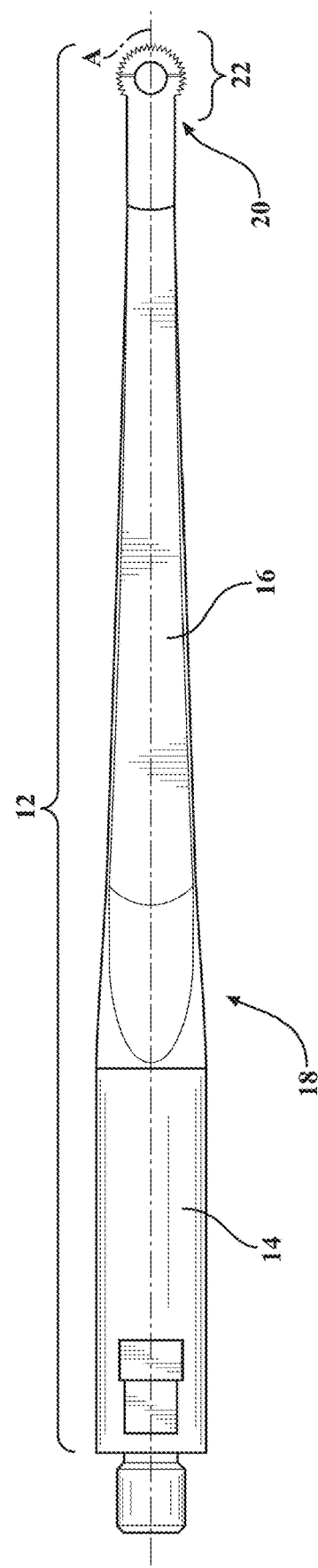
FIG. 2 is a top plan view of the ultrasonic tip of FIG. 1.
Figure 3:
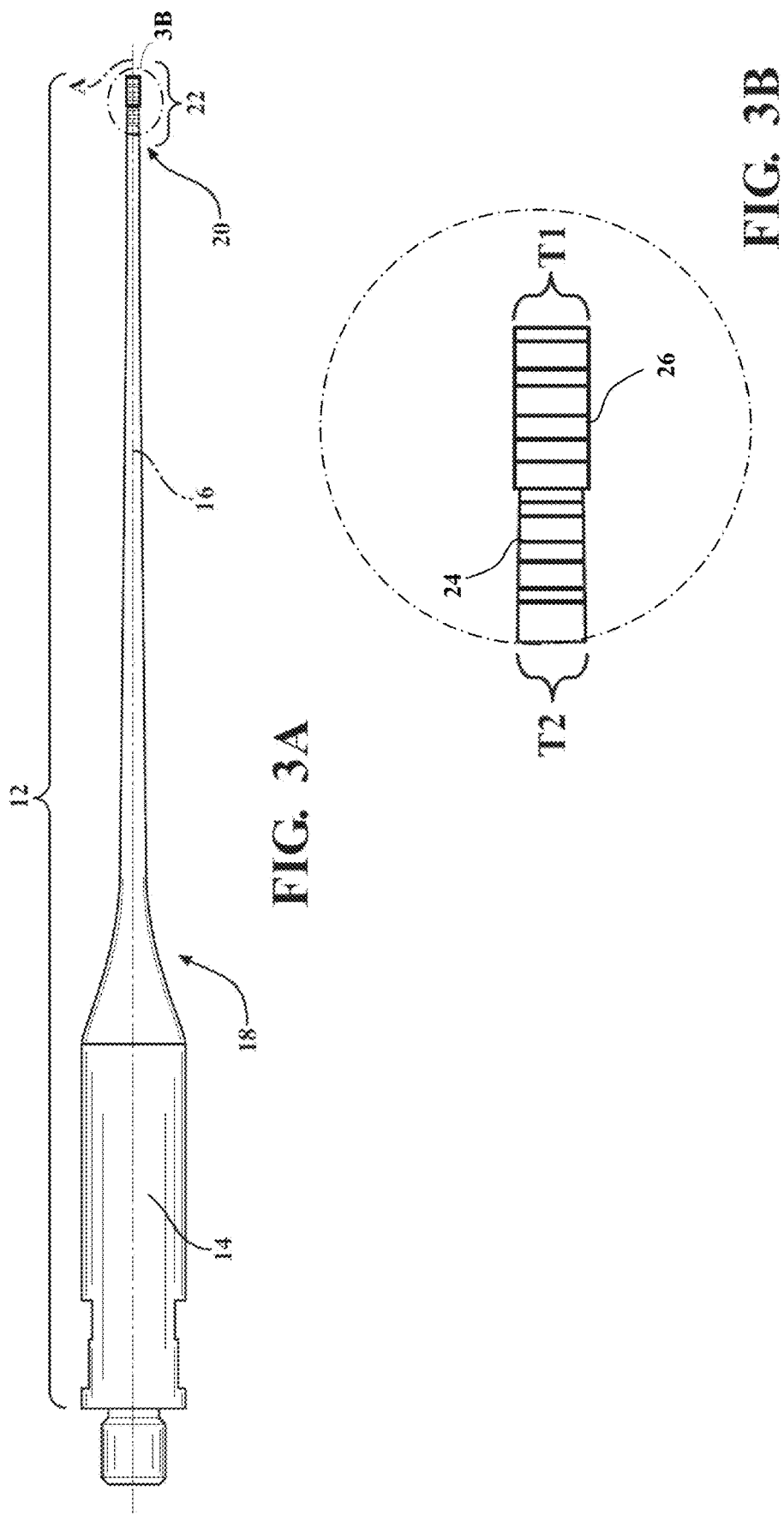
FIG. 3A is a side plan view of the ultrasonic tip of FIG. 1.
FIG. 3B is a detailed view of a cutting portion of the ultrasonic tip of FIG. 3A within circle 3B.

FIGS. 2 and 3A illustrate a top plan view and a side plan view, respectively, of the ultrasonic tip 10 of FIG. 1. In some configurations, a length of the body 16 is at least twice a length of the base 14. In one configuration, a length of a combination of the first portion 18 and the second portion 20 of the body 16 is at least half of a total length of the shaft 12. In yet another configuration, the length of a combination of the first portion 18 and the second portion 20 of the body 16 is greater than half of a length of the shaft 12. In an exemplary embodiment, the length of a combination of the first portion 18 and the second portion 20 is sixty percent of the total length of the shaft 12. FIG. 3B illustrates a detailed view of the cutting portion 22 of the ultrasonic tip 10 of FIG. 3A within circle 3B, described in more detail below.

Figure 4:
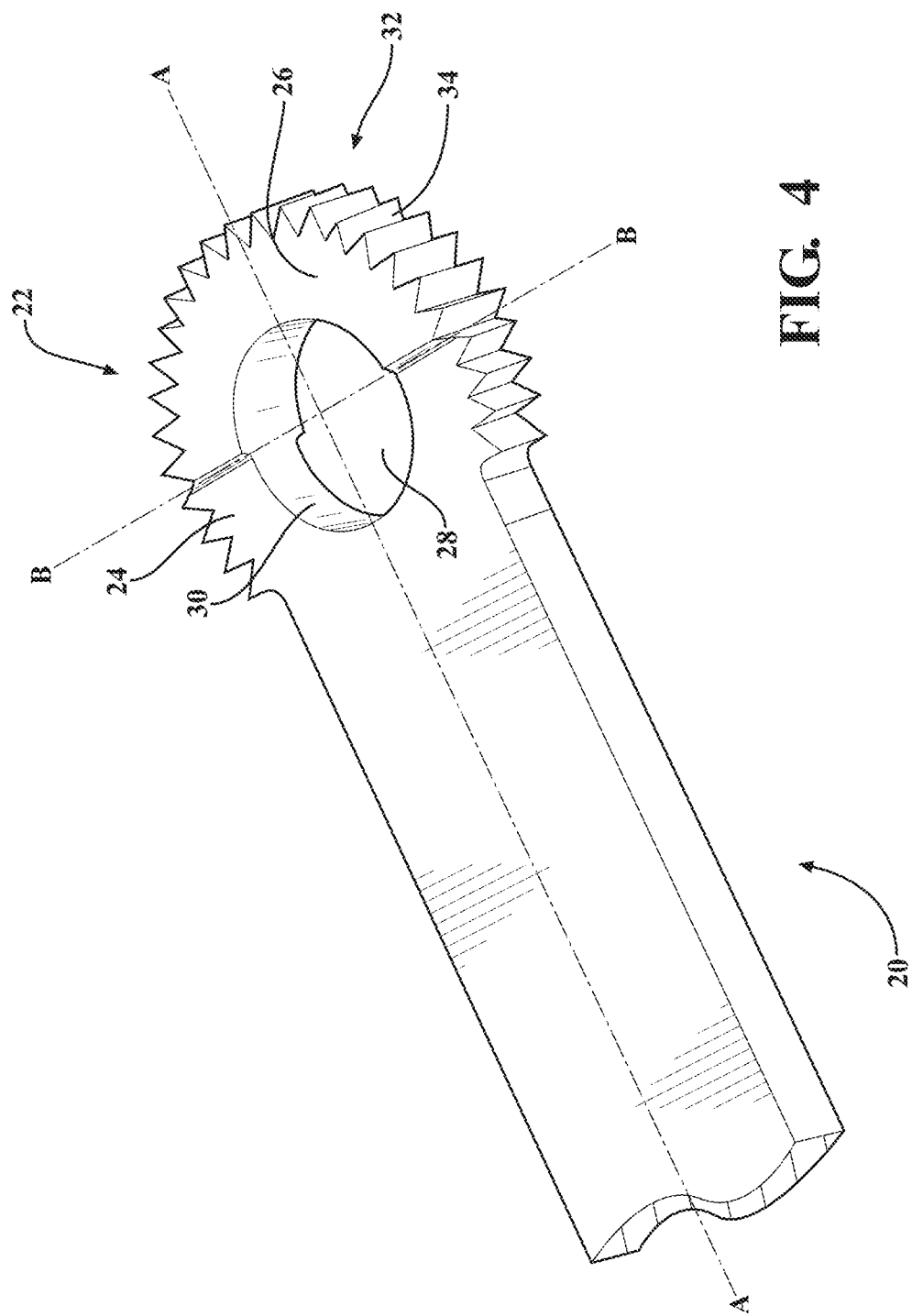
FIG. 4 is a partial perspective view of a cutting portion of the ultrasonic tip of FIG. 1.

FIG. 4 illustrates a partial perspective view of a cutting portion of the ultrasonic tip of FIG. 1. The cutting portion 22 comprises a neck 24 and a head 26. The head 26 extends radially from the longitudinal axis A. The head 26 is coupled to the neck 24.

An aperture 28 is disposed between the head 26 and the neck 24 to define an inner circumferential surface 30. In other words, the aperture 28 may be partially defined by the material forming the head 26 and the neck 24. The aperture 28 may be circular in shape or D-shaped, and may be a through-hole. The cross-sectional shape of the aperture 28 may be consistent across axis B. The head 26 and the neck 24 form an outer circumferential surface 32. The outer circumferential surface 32 is disposed radially about a center of the aperture 28 and extends at least 180 degrees relative to a central axis B of the aperture. The central axis B may be transverse to the longitudinal axis A of the shaft 14, and may be perpendicular in some embodiments. In configurations where the aperture is circular, the inner circumferential surface 30 may be concentric with the outer circumferential surface 32. In many configurations, both the inner circumferential surface 30 and the outer circumferential surface 32 may be arc-shaped in at least one dimension. The outer circumferential surface 32 includes a plurality of cutting teeth, one of which is labeled 34.

Referring again to FIG. 3B, in certain configurations, the outer circumferential surface 32 has a first thickness T1 at the head 26 and a second thickness T2 at the neck 24, wherein the first thickness T1 is greater than the second thickness T2 to allow the insertion of a portion of the head 26 and the neck 26 into a cutting site. The staged thickness of the neck 24 and head 26 of the cutting portion 22 improves the reach of the cutting portion 22 into the cutting site.

Figure 5:
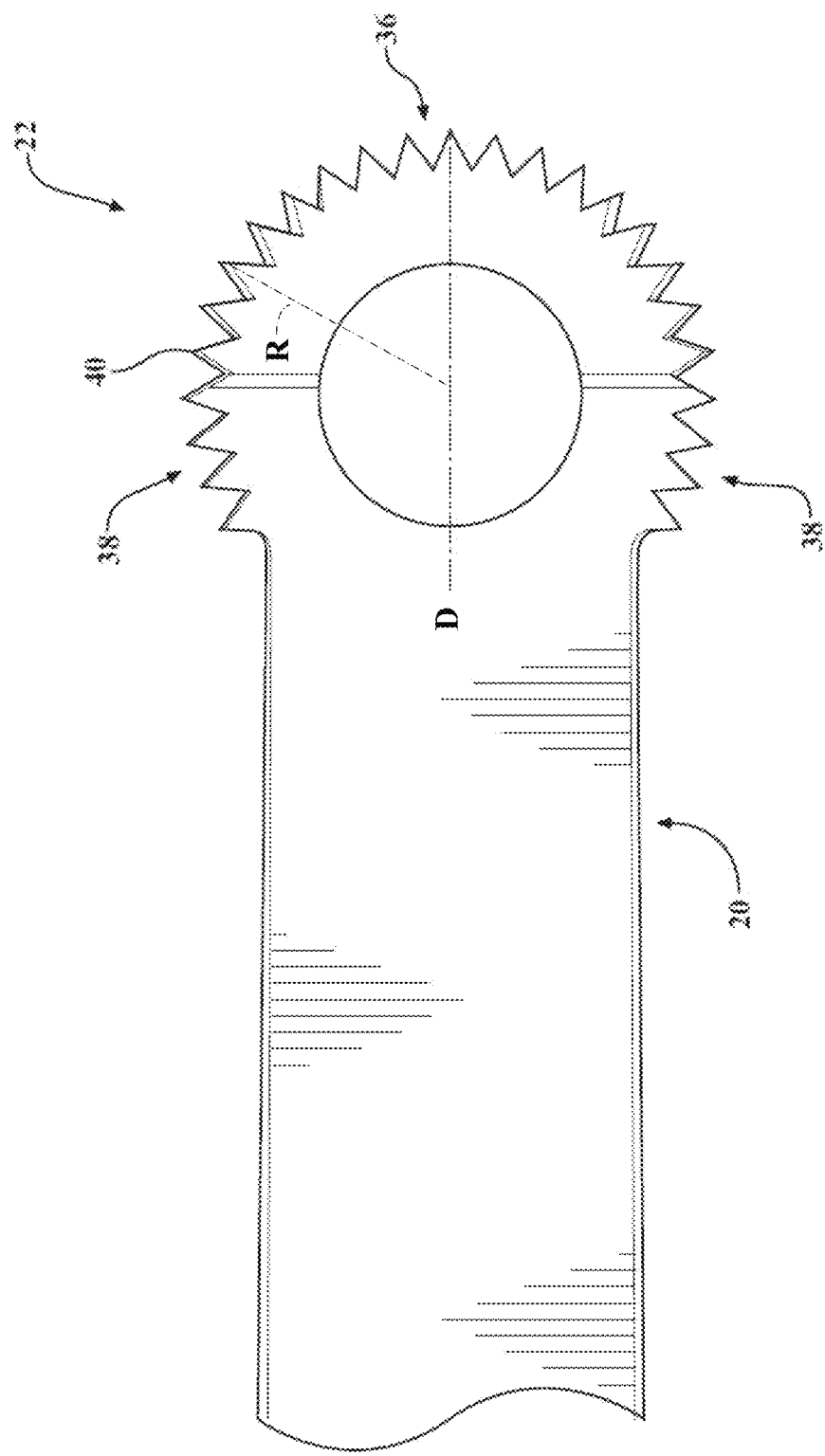
FIG. 5 is a partial plan view of a cutting portion of the ultrasonic tip of FIG. 1.

FIG. 5 illustrates a partial plan view of a cutting portion of the ultrasonic tip of FIG. 1. In some configurations, the plurality of cutting teeth 34 comprise a first set of cutting teeth 36 disposed on the head 26 and a second set of cutting teeth 38 disposed on the neck 24. At least one cutting tooth of the first set of cutting teeth 36 has a thickness greater than a thickness of at least one cutting tooth of the second set of cutting teeth 38. In some configurations, the ultrasonic tip 10 is free from teeth cutting teeth except those plurality of cutting teeth 34 disposed on the outer circumferential surface 32. In such a configuration, the only teeth present on the ultrasonic tip are those disposed on an arc or radius. A tip 40 of each of the plurality of teeth 34 points away from the central axis B. In one configuration, all of the tips 40 of any of the plurality of teeth 34 of the ultrasonic tip 10 are positioned along an arc extending at a constant radius R of the cutting portion, from a center of the aperture 28. In one configuration, a diameter D of the cutting portion 22 is less than or equal to 5 millimeters.

Figure 6:
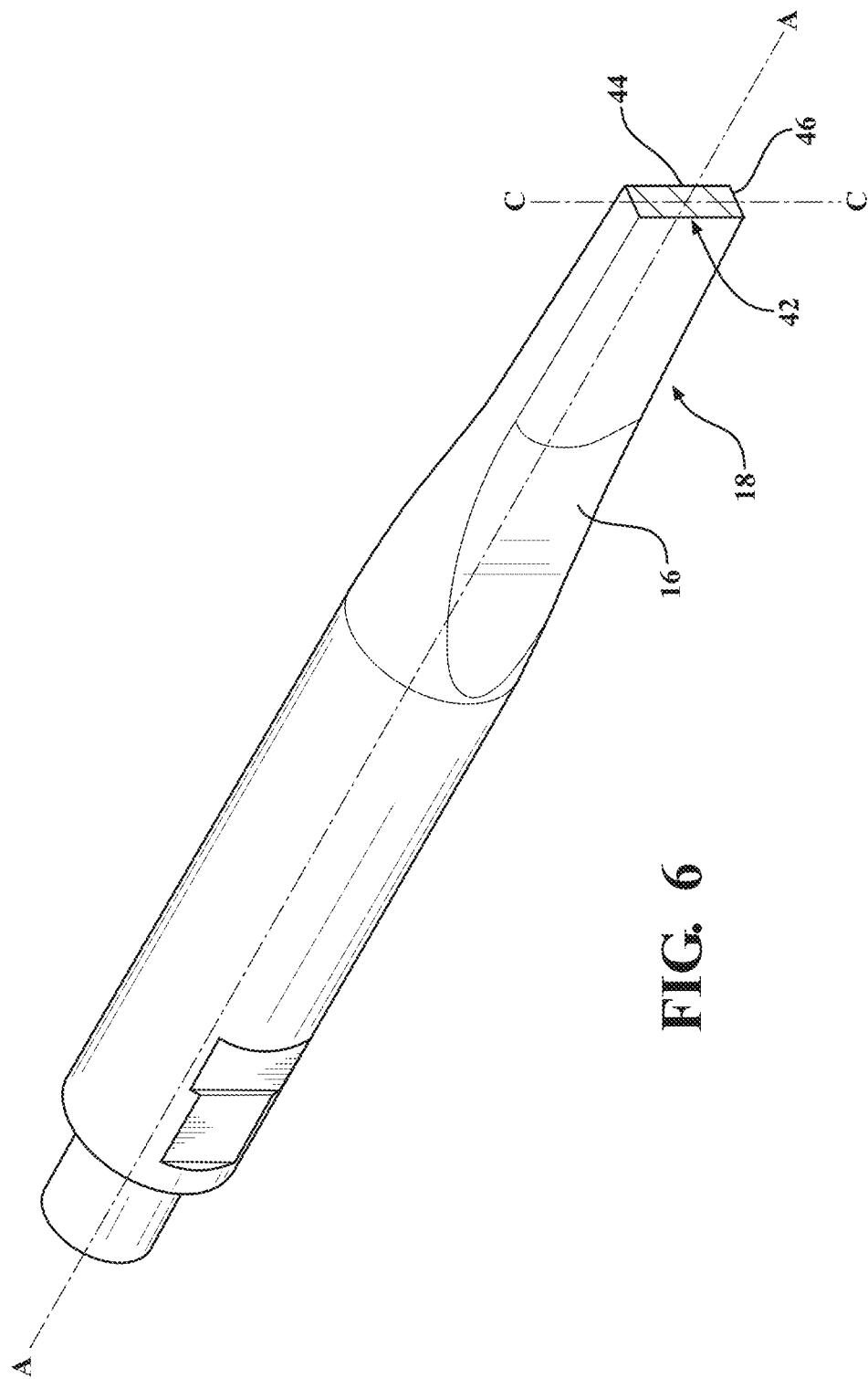
FIG. 6 is a cross-sectional perspective view of a first portion of the ultrasonic tip of FIG. 1.

Referring now to FIG. 6, a cross-sectional perspective view of the first portion 18 of the ultrasonic tip 10 of FIG. 1 is shown. The body 16 has a rectangular-shaped cross-section 42 on an axis C that is perpendicular to the longitudinal axis A at the first portion 18. In some configurations, a height 44 of the rectangular-shaped cross-section 42 at the first portion 18 is at least three times greater than a width 46 of the rectangular-shaped cross section 42.

Figure 7:
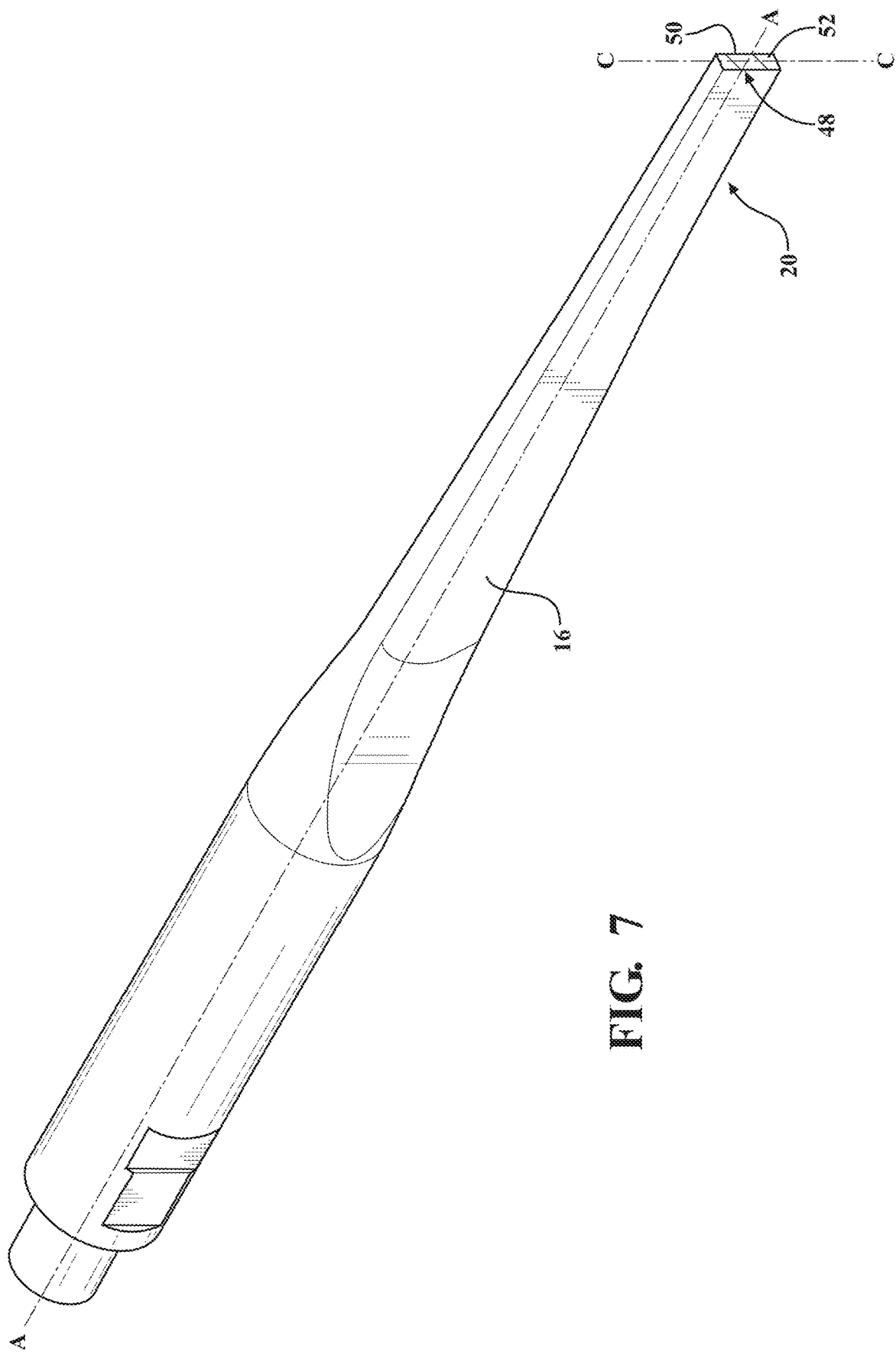
FIG. 7 is a cross-sectional perspective view of a second portion of the ultrasonic tip of FIG. 1.

Referring now to FIG. 7, a cross-sectional perspective view of the second portion 20 of the ultrasonic tip 10 of FIG. 1 is shown. The body 16 has a rectangular-shaped cross-section 48 on an axis C that is perpendicular to the longitudinal axis A at the second portion 20. In some configurations, a height 50 of the rectangular-shaped cross-section 48 at the second portion 20 is at least three times greater than a width 52 of the rectangular shaped cross-section 48. In this configuration illustrated in FIGS. 6-7, the height 44 is greater than the height 50, and the width 46 is greater than the width 52.

An advantage of the reduction in the overall thickness of the body 16 of the ultrasonic tip 10 is that the body 16 is more flexible laterally. Therefore, if the ultrasonic tip 10 is wedged and the surgeon applies a lateral force on it, creating bending, the stress is concentrated in the body 16 instead of the cutting portion 22, which improves the overall strength of the shaft 12 and reduces the chance of breakage of the cutting portion 22.

Figure 8:
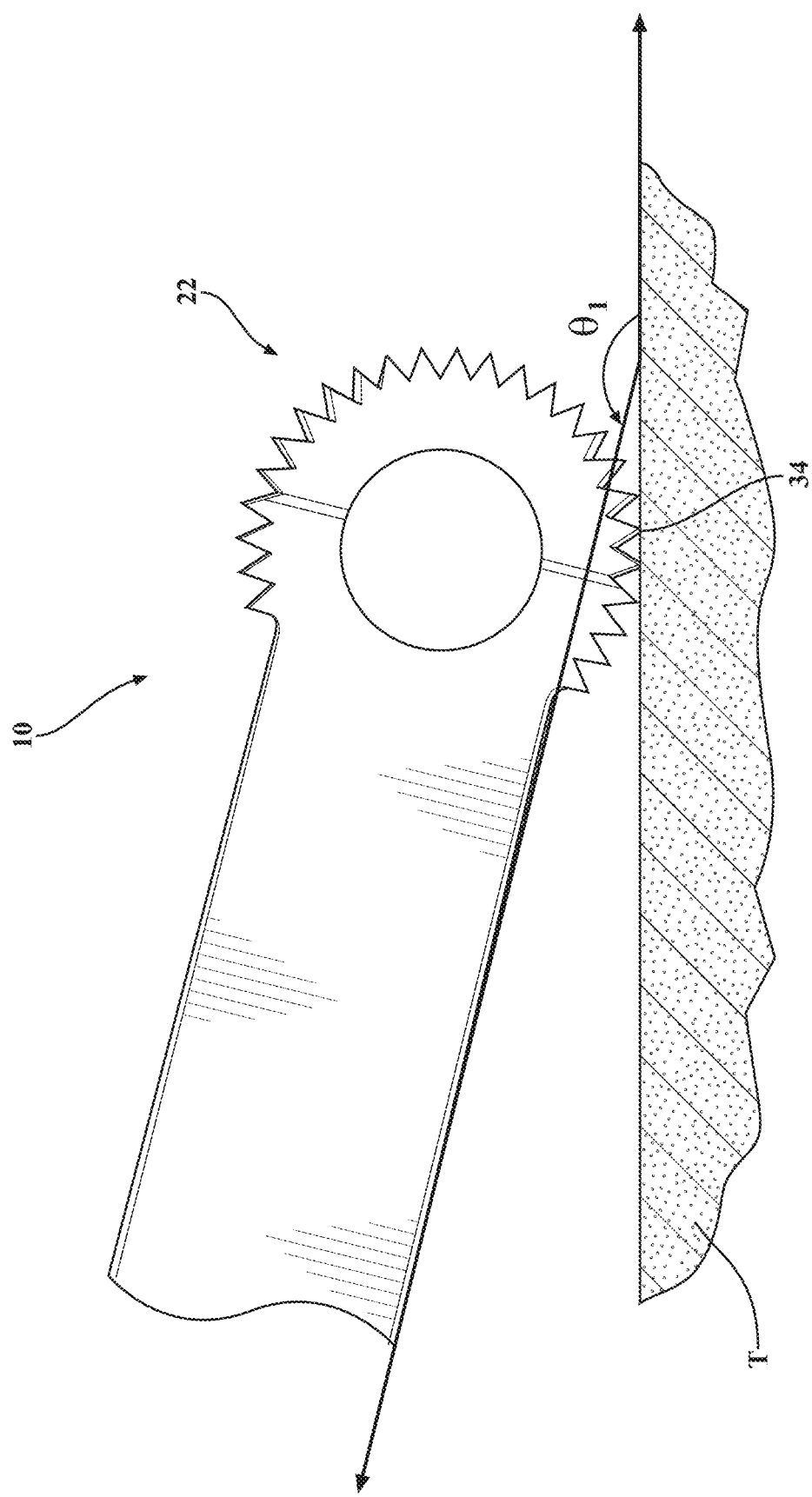
FIG. 8 is a partial plan view of a cutting portion of the ultrasonic tip of FIG. 1 shown in contact with tissue of a patient at a first angle.

FIG. 8 illustrates a partial plan view of the cutting portion 22 of the ultrasonic tip 10 shown in contact with tissue T of a patient at a first angle. As previously mentioned, the ultrasonic tip 10 is used to cut tissue, such as bone, during a surgical procedure. A method of operating the ultrasonic tip 10 includes moving the ultrasonic tip 10 into contact with tissue T at a surgical site of a patient. The ultrasonic tip 10 may cut the tissue T against a first positive rake angle $\theta_1$ of the cutting portion 22. The first positive rake angle $\theta_1$ may be at least 90 degrees and less than or equal to 150 degrees. At the first positive rake angle $\theta_1$, a maximum number or amount of the plurality of teeth 34 may be in contact with the tissue T. For example, in one configuration, a maximum of five of the plurality of teeth 34 are in contact with the tissue T at the first positive rake angle $\theta_1$. In other configurations, a maximum percentage of the plurality of teeth 34 may be in contact with the tissue T at the first positive rake angle $\theta_1$. For example, in one configuration, a maximum of twenty percent of the plurality of teeth 34 are in contact with the tissue T at the first positive rake angle $\theta_1$.

Figure 9:
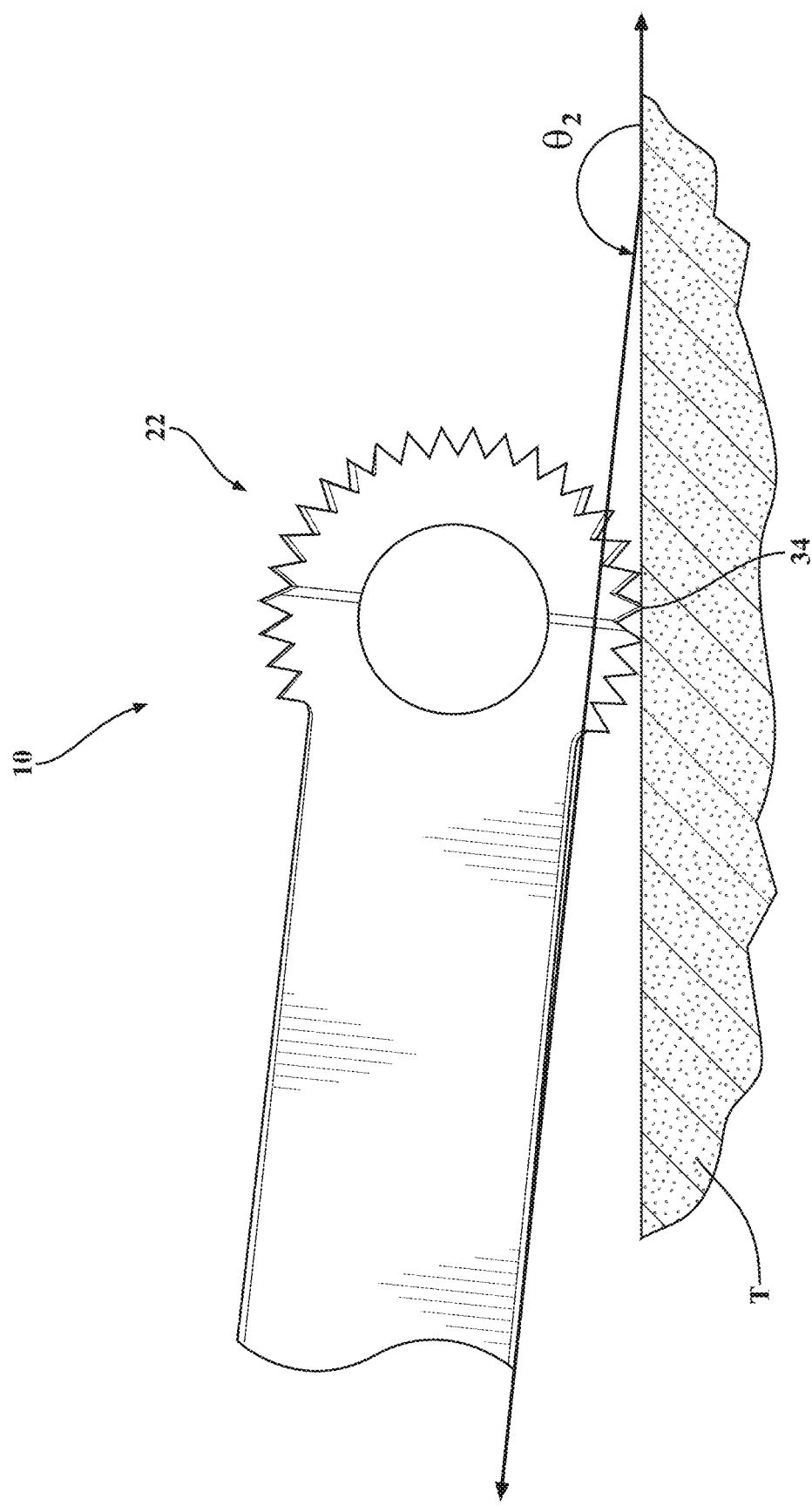
FIG. 9 is a partial plan view of a cutting portion of the ultrasonic tip of FIG. 1 shown in contact with tissue of a patient at a second angle.

FIG. 9 illustrates a partial plan view of the cutting portion 22 of the ultrasonic tip 10 shown in contact with the tissue T of a patient at a second angle. The ultrasonic tip 10 may then cut the tissue T against a second positive rake angle $\theta 2$ of the cutting portion 22. The second positive rake angle $\theta 2$ is greater than the first positive rake angle $\theta_1$, being at least 149 degrees and less than or equal to 180 degrees. At the second positive rake angle $\theta_2$, a maximum number or amount of the plurality of teeth 34 may be in contact with the tissue T. For example, in one configuration, a maximum of five of the plurality of teeth 34 are in contact with the tissue T at the second positive rake angle $\theta_2$. In other configurations, a maximum percentage of the plurality of teeth 34 may be in contact with the tissue T at the second positive rake angle $\theta_2$. For example, in one configuration, a maximum of twenty percent of the plurality of teeth 34 are in contact with the tissue T at the second positive rake angle $\theta_2$. Thus, the same number or amount of the plurality of teeth 34 are in contact with the tissue T at both the first positive rake angle $\theta_1$ and the second positive rake angle $\theta_2$.

In the embodiments described above and shown in the Figures, an advantage to the described ultrasonic tip 10 is improved strength of the teeth 34. Stress is concentrated on the teeth 34 more evenly due to the circular shape of the cutting portion 22. In addition, the serration length of each tooth 34 is much shorter than serrated teeth on traditional ultrasonic tips, which eliminates stress concentration on the tip 10, which in turn allows the tip 10 to be run at higher displacement and makes it less sensitive to wedging. By way of example, the serration length of the described embodiments may be less than 4 mm, compared to a serration length in other tips of about 12 mm.

The flexible body 16, combined with the staged thickness of the cutting portion 22, further improves the reach of the cutting portion 22 into the cutting site. The overall reach of the tip 10 is increased to at least 25 mm, which is about twice the reach of other ultrasonic tips.

However, the reduction in overall thickness of the body 16 means use of a lumen for irrigation and aspiration is difficult. Therefore, providing cooling to the cutting site without the use of a lumen in the body 16 relies solely on irrigation. Thus, the irrigation fluid must be carried to the cutting side, and then debris must be cleared out during cutting. The irrigation fluid tends to stick to the ultrasonic tip 10 by capillarity. However, normally, when digging a deep groove, the fluid would not reach the cutting portion 22, because the sides of the tip 10 would be in contact with bone walls. The combination of the wider cutting portion 22 and the narrower body 16 in the embodiments described and shown allows the fluid to reach the cutting site more easily by creating more space for the fluid to move along the tip 10 to the cutting portion 22. Once the fluid reaches the aperture 28, the inner circumferential surface 30 then creates a thermal exchange surface that is close to the teeth 34 of the cutting portion 22. Additionally, the aperture 28 acts as a storing cavity for debris and fluid that builds up during cutting. The shape of the staged cutting portion 22 assists with retaining fluid in the aperture 28, with increased thickness in the head 26 as compared to the thickness of the neck 24 (see FIG. 3B, illustrating the first thickness T1 at the head 26 and the second thickness T2 at the neck 24). In addition, because the cutting portion 22 is wider than the narrower body 16, the fluid is directed down the narrower body 16 to collect in the aperture 28. The more fluid that pools in the aperture 28, the greater the cooling due to thermal exchange between the inner circumferential surface 30 and the outer circumferential surface 32 and the teeth 34. In addition, because the aperture 28 is a through-hole, it reduces the overall surface area of the cutting portion 22 that is in contact with tissue, which reduces heating at the cutting site. Moreover, it is easier and more cost-effective to manufacture a tip 10 with an aperture 28 as opposed to a common "dish" design that comprises a groove instead of a through-hole.

Yet a further advantage is that the circular or arc shape of the cutting portion 22 ensures that a similar amount of the overall number of teeth 34 will be in contact with tissue at any given time, regardless of the rake angle of the tip 10 in relation to the tissue T. When too few teeth 34 are in contact with the tissue T, there is high individual stress on each tooth 34, but the tip 10 has greater reach and access to the cutting site. When too many teeth 34 are in contact with the tissue T, there is low individual stress on each tooth 34, but the tip 10 has reduced reach and access to the cutting site. Accordingly, the advantage of the embodiments shown and described is that a certain number of teeth 34 will be in contact with tissue T at any angle, such that the access and reach of the tip 10 will not be minimized due to rake angle, nor will there be higher individual stress on certain teeth 34 due to rake angle. The result is more consistent performance of the cutting portion 22.

Clauses covering additional configurations of the cutting tips and methods of operating the same, described above:

i. An ultrasonic tip comprising: a shaft including a base and a body, the base having a circular-shaped cross-section, the body comprising a first portion and a second portion, wherein the body is coupled to the base at the first portion and said body extends from said first portion to said second portion along a longitudinal axis, and said second portion includes a cutting portion, wherein a length of the body is at least twice a length of the base; the body having a rectangular-shaped cross-section on an axis that is perpendicular to the longitudinal axis at said first portion and at said second portion, wherein: a first height of the rectangular-shaped cross-section at the first portion is at least three times greater than a first width of the rectangular-shaped cross section, and a second height of the rectangular-shaped cross-section at the second portion is at least three times greater than a second width of the rectangular shaped cross-section.

ii. The ultrasonic tip of clause i, wherein the first height is greater than the second height.

iii. The ultrasonic tip of clause i, wherein the first width is greater than the second width.

iv. The ultrasonic tip of clause i, wherein the cutting portion comprises a neck and a head, said head extending radially from the longitudinal axis and coupled to said neck.

v. The ultrasonic tip of clause iv, wherein a circular aperture is disposed between the head and the neck to define an inner circumferential surface.

vi. The ultrasonic tip of clause iv, wherein the head and the neck form an outer circumferential surface comprising a plurality of cutting teeth.

vii. The ultrasonic tip of clause v, wherein the outer circumferential surface has a first thickness at the head and a second thickness at the neck.

viii. The ultrasonic tip of clause vii, wherein the first thickness is greater than the second thickness.

ix. The ultrasonic tip of clause v, wherein the aperture is a through-hole.

x. The ultrasonic tip of clause vi, wherein the outer circumferential surface is disposed radially about a center of the aperture and extends more than 180 degrees relative to a central axis of the aperture.

xi. The ultrasonic tip of clause vi, wherein the ultrasonic tip is free from teeth except those disposed on the outer circumferential surface.

xii. The ultrasonic tip of clause i, wherein a diameter of the cutting portion is less than or equal to 5 millimeters.

xiii. The ultrasonic tip of clause i, wherein a length of a combination of the first portion and the second portion of the body is at least half of a length of the shaft.

xiv. The ultrasonic tip of clause i, wherein a length of a combination of the first portion and the second portion of the body is greater than half of a length of the shaft.

xv. The ultrasonic tip of clause i, wherein the base is cylindrical.

xvi. The ultrasonic tip of clause i, wherein the body is solid.

xvii. The ultrasonic tip of clause i, wherein the shaft is integral, unitary, and one-piece.

xviii. An ultrasonic cutting tip comprising: a shaft having a base portion, a neck portion, and a head portion, said neck portion being disposed between said base portion and said head portion along a longitudinal axis, said head portion comprising a base and a crown coupled to said base and being formed with a plurality of teeth, and wherein a thickness of said crown is greater than a thickness of the base and a thickness of the neck portion to allow the insertion of a portion of said base and said neck into a cut by said head portion, and said head portion defining an aperture, and the plurality of cutting teeth comprise a first set of cutting teeth and a second set of cutting teeth, the first set of cutting teeth disposed on said crown and the second set of cutting teeth disposed on said base portion, at least one cutting tooth of the first set of cutting teeth has a thickness greater than a thickness of at least one cutting tooth of the second set of cutting teeth.

xix. The ultrasonic cutting tip of clause xviii, wherein the aperture has an axis that is transverse the longitudinal axis of said shaft.

xx. The ultrasonic cutting tip of clause xviii, wherein the base portion is solid.

xxi. The ultrasonic cutting tip of clause xviii, wherein the shaft is integral, unitary, and one-piece.

xxii. The ultrasonic cutting tip of clause xviii, wherein the base portion has a rectangular-shaped cross-section at a first portion and at a second portion, wherein: a first height of the rectangular-shaped cross-section at the first portion is at least three times greater than a first width of the rectangular-shaped cross section, and a second height of the rectangular-shaped cross-section at the second portion is at least three times greater than a second width of the rectangular shaped cross-section.

xxiii. The ultrasonic cutting tip of clause xxii, wherein the first height is greater than the second height.

xxiv. The ultrasonic cutting tip of clause xxii, wherein the first width is greater than the second width.

xxv. The ultrasonic cutting tip of clause xxii, wherein a length of a combination of the first portion and the second portion is at least half of a length of the shaft.

xxvi. The ultrasonic cutting tip of clause xxii, wherein a length of a combination of the first portion and the second portion is greater than half of a length of the shaft.

xxvii. The ultrasonic cutting tip of clause xviii, wherein a diameter of the head portion and the neck portion is less than or equal to 5 millimeters.

xxviii. The ultrasonic cutting tip of clause xviii, wherein the aperture is circular.

xxix. The ultrasonic cutting tip of clause xviii, wherein the aperture is a through-hole.

xxx. The ultrasonic cutting tip of clause xviii, wherein the head portion defines an outer circumferential surface comprising the plurality of cutting teeth.

xxxi. The ultrasonic cutting tip of clause xxx, wherein the outer circumferential surface is disposed radially about a center of the aperture and extends more than 180 degrees relative to a central axis of the aperture.

xxxii. The ultrasonic cutting tip of clause xxx, wherein the aperture defines an inner circumferential surface.

xxxiii. The ultrasonic cutting tip of clause xxxii, wherein the inner circumferential surface is concentric with the outer circumferential surface.

xxxiv. The ultrasonic cutting tip of clause xviii, wherein the ultrasonic cutting tip is free from teeth except those disposed on the head portion.

xxxv. The ultrasonic cutting tip of clause xviii, wherein a tip of each of the plurality of teeth points away from the axis of the aperture.

xxxvi. A method of operating an ultrasonic cutting tip, the method including the steps of: moving the ultrasonic cutting tip into contact with tissue at a surgical site of a patient, the ultrasonic cutting tip having a shaft including a base portion, a neck portion, and a head portion, said neck portion being disposed between said base portion and said head portion along a longitudinal axis, said head portion and neck portion being formed with a plurality of teeth, cutting the tissue against a first positive rake angle of the head portion, wherein a maximum of twenty percent of the plurality of teeth are in contact with the tissue at the first positive rake angle; and cutting the tissue against a second positive rake angle of the head portion, wherein the second positive rake angle is greater than the first positive rake angle, and wherein a maximum of twenty percent of the plurality of teeth are in contact with the tissue at the second positive rake angle.

xxxvii. The method of clause xxxvi, wherein the first positive rake angle is at least 90 degrees and less than or equal to 150 degrees.

xxxviii. The method of clause xxxvi, wherein the second positive rake angle at least 149 degrees and less than or equal to 180 degrees.

xxxix. An ultrasonic tip comprising: a shaft including a base and a body, the body comprising a first portion and a second portion, wherein the body is coupled to the base at the first portion and said body extends from said first portion to said second portion along a longitudinal axis, said second portion includes a cutting portion having a plurality of teeth, said second portion comprising a neck, and a head extending radially from the longitudinal axis, and coupled to said neck, wherein an aperture is disposed between the head and the neck to define an inner circumferential surface, and wherein all of the tips of any teeth of the ultrasonic cutting tip are positioned along an arc extending at a constant radius of the cutting portion from a center of said aperture.

xl. A method of operating an ultrasonic cutting tip, the method including the steps of moving the ultrasonic cutting tip into contact with tissue at a surgical site of a patient, the ultrasonic cutting tip having a shaft including a base portion, a neck portion, and a head portion, said neck portion being disposed between said base portion and said head portion along a longitudinal axis, said head portion and neck portion being formed with a plurality of teeth, cutting the tissue against a first positive rake angle of the head portion, wherein a maximum of five of the plurality of teeth are in contact with the tissue at the first positive rake angle; and cutting the tissue against a second positive rake angle of the head portion, wherein the second positive rake angle is greater than the first positive rake angle, and wherein a maximum of five of the plurality of teeth are in contact with the tissue at the second positive rake angle.

xli. The method of clause xl, wherein the first positive rake angle is at least 90 degrees and less than or equal to 150 degrees.

xlii. The method of clause xli, wherein the second positive rake angle at least 149 degrees and less than or equal to 180 degrees.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. An ultrasonic tip comprising:
a shaft including a base and a body, the body comprising a first portion and a second portion, wherein the body is coupled to the base at the first portion and the body extends from the first portion to the second portion along a longitudinal axis,
wherein the second portion includes a cutting portion comprising a neck, and a head extending radially from the longitudinal axis, and coupled to the neck,
wherein a circular aperture is disposed between the head and the neck to define a continuous inner circumferential surface for collecting fluid during a procedure,
wherein a length of the body is at least twice a length of the base, and the body has a rectangular-shaped cross-section on an axis that is perpendicular to the longitudinal axis at the first portion and at the second portion,
wherein a first height of the rectangular-shaped cross-section at the first portion is at least three times greater than a first width of the rectangular-shaped cross-section at the first portion, and
wherein a second height of the rectangular-shaped cross-section at the second portion is at least three times greater than a second width of the rectangular-shaped cross-section at the second portion.

2. The ultrasonic tip of claim 1, wherein the head and the neck form an outer circumferential surface comprising a plurality of cutting teeth, the outer circumferential surface having a first thickness at the head and a second thickness at the neck, wherein the first thickness is greater than the second thickness.

3. The ultrasonic tip of claim 2, wherein the outer circumferential surface is disposed radially about a center of the aperture and extends more than 180 degrees relative to a central axis of the aperture.

4. The ultrasonic tip of claim 2, wherein the ultrasonic tip is free from teeth except those disposed on the outer circumferential surface.

5. The ultrasonic tip of claim 1, wherein the base is cylindrical.

6. The ultrasonic tip of claim 1, wherein the body is solid.

7. The ultrasonic tip of claim 1, wherein the shaft is integral, unitary, and one-piece.

8. The ultrasonic tip of claim 1, wherein the aperture is a through-hole.

9. The ultrasonic tip of claim 1, wherein the first height is greater than the second height.

10. The ultrasonic tip of claim 1, wherein the first width is greater than the second width.

11. The ultrasonic tip of claim 1, wherein a length of a combination of the first portion and the second portion of the body is at least half of a length of the shaft.

12. The ultrasonic tip of claim 1, wherein a length of a combination of the first portion and the second portion of the body is greater than half of a length of the shaft.

13. The ultrasonic tip of claim 1, wherein a diameter of the cutting portion is less than or equal to 5 millimeters.

14. An ultrasonic tip comprising:
a shaft including a base and a body, the base having a circular-shaped cross-section, and the body comprising a first portion and a second portion, wherein the body is coupled to the base at the first portion and the body extends from the first portion to the second portion along a longitudinal axis, and the second portion includes a cutting portion, the body having a rectangular-shaped cross-section at the first and second portions, the rectangular-shaped cross-section at each of the first and second portions being on an axis that is perpendicular to the longitudinal axis at the first portion and at the second portion, and wherein:
a first height of the rectangular-shaped cross-section at the first portion is at least three times greater than a first width of the rectangular-shaped cross-section at the first portion, and
a second height of the rectangular-shaped cross-section at the second portion is at least three times greater than a second width of the rectangular-shaped cross-section at the second portion; and
wherein the first height is greater than the second height.

15. The ultrasonic tip of claim 14, wherein the first width is greater than the second width.

16. The ultrasonic tip of claim 14, wherein the cutting portion comprises a neck and a head, the head extending radially from the longitudinal axis and coupled to the neck.

17. The ultrasonic tip of claim 14, wherein a diameter of the cutting portion is less than or equal to 5 millimeters.

18. The ultrasonic tip of claim 14, wherein a length of a combination of the first portion and the second portion of the body is at least half of a length of the shaft.

19. The ultrasonic tip of claim 14, wherein a length of a combination of the first portion and the second portion of the body is greater than half of a length of the shaft.

* * * * *